(12) United States Patent  (10) Patent No.: US 8,574,281 B2
Vracknos  (45) Date of Patent: Nov. 5, 2013

(54) METHOD AND APPARATUS OF PARAFFIN TREATMENT OF THE SKIN

(76) Inventor: Nicholas Vracknos, Healesville (AU)

( * ) Notice: Subject to any disclaimer, the term of this patent is extended or adjusted under 35 U.S.C. 154(b) by 709 days.

(21) Appl. No.: 12/559,454

(22) Filed: Sep. 14, 2009

(65) Prior Publication Data

US 2010/0065081 A1    Mar. 18, 2010

Related U.S. Application Data

(60) Provisional application No. 61/096,691, filed on Sep. 12, 2008.

(51) Int. Cl.
*A61F 7/10* (2006.01)
*A43B 7/02* (2006.01)
*A61F 7/00* (2006.01)
*B65D 33/00* (2006.01)

(52) U.S. Cl.
USPC ............ 607/108; 607/96; 607/111; 607/114; 36/2.6; 132/118; 132/285; 132/320; 383/901

(58) Field of Classification Search
USPC ........ 607/108, 111, 96, 114; 36/2.6; 132/118, 132/285, 320; 383/901
See application file for complete search history.

(56) References Cited

U.S. PATENT DOCUMENTS

| | | | |
|---|---|---|---|
| 5,891,116 A * | 4/1999 | Mast | 604/290 |
| 6,146,413 A * | 11/2000 | Harman | 607/111 |
| 6,174,319 B1 * | 1/2001 | Desnos | 606/133 |
| 2004/0102823 A1 * | 5/2004 | Schnoor | 607/96 |
| 2004/0107475 A1 * | 6/2004 | Gogarty | 2/159 |
| 2009/0227967 A1 * | 9/2009 | Donovan et al. | 604/291 |

* cited by examiner

*Primary Examiner* — Linda Dvorak
*Assistant Examiner* — Jared W Pike
(74) *Attorney, Agent, or Firm* — Donn K. Harms

(57) ABSTRACT

A device and method for the sanitary provision of wax to the skin of patrons. Paraffin wax containers shaped to conform to the patrons face, hands, and feet provide individual reservoirs of paraffin which are heated and subsequently applied to the patron's body. Exothermic pouches are provided to heat the individual portions of paraffin wax housed in the body-part-shaped containers.

6 Claims, 3 Drawing Sheets

METHOD AND APPARATUS OF PARAFFIN TREATMENT OF THE SKIN

This application claims priority to U.S. Provisional Patent Applications No. 61/096,691 filed on Sep. 12, 2008.

BACKGROUND OF THE INVENTION

1. Field of the Invention

The present invention relates to the treatment of skin employing paraffin wax or similarly available material applicable to the skin after reaching melting temperature.

More particularly it relates to a device and method for heating individual sterile packages shaped to conform to a body part of the patron receiving the sterile individually applicable paraffin treatments.

2. Prior Art

A popular cosmetic and medicinal treatment for the skin is provided by the application of heated paraffin to various areas of the body in coatings or masks such as the hands, arms, elbows, and in coatings on the face for facials. Conventionally, paraffin wax is heated to approximately 53 degrees Celsius in a suitable deep dish wax heater. Once the wax has substantially reached this temperature, the appropriate body part of the user is initially sprayed or wiped with a disinfectant preparation. Once the body part has been so wiped, the body part to be treated is then repeatedly dipped into the melted wax supply. This concurrently delivers a warm, very pleasant and soothing sensation while the body part is being coated. During this process, a generous layer of wax is accumulated on the body part being treated. In the case of the customer's feet or hands, once so coated, they are inserted into a plastic type bag which is then wrapped in a towel or similar mitt to maintain warmth for approximately twenty minutes during a rest and treatment interval. During this rest interval the wax relaxes muscles of the hands. Concurrently the wax itself is allowed to deeply penetrate the heat-expanded pores of the skin which promotes skin hydration. At the end of this process, the mitts and protective bags are removed and the coated wax on the body part is then peeled away. The result to the user is skin with an enhanced feel and finish and which is more fully hydrated.

In addition to the hydration and softness improvement of the skin so treated, other benefits are provided the user. The application of heated paraffin wax and the subsequent relaxation period with the heated wax applied also increases blood circulation to the area and allows for the restoration of improved skin color. The heat provided by the paraffin can also be employed to ease stiffness and discomfort of joints associated with injury, arthritis, overworked muscles, and other ailments.

Conventionally, in preparing for the treatment, the paraffin wax is heated to approximately 53 degrees Celsius in a suitable deep dish wax heater. Prior to application of the wax to the body, the intended body part is initially sprayed or wiped with a disinfectant preparation in an attempt to prevent germ or other contamination of the reservoir of paraffin. Following the disinfectant treatment, the body part is then repeatedly dipped into the paraffin reservoir to achieve a coating on the body part. Through one or a plurality of these subsequent dips into the reservoir, a generous layer of wax is accumulated on the body part being treated.

In the case of the feet or hands being treated, once the wax layer has accumulated, they are then directly inserted into a plastic type bag and then inserted into a towel or similar mitt or cover for approximately twenty minutes. Having cooled after the elapsed time, the wax is then easily peeled off leaving an amazing feel and finish to the skin.

However, this method of dipping and coating body parts, even after the application of disinfectant, has been determined to be fraught with peril from contamination of the wax reservoir by users. Many germs, bacteria, and viruses have been found to survive not only the disinfectant wipe, but also the heat in the reservoir of paraffin. Some pathogens actually thrive in such an environment.

The same is true of other temporary skin coating material with similar skin and body enhancement properties such as mud, oil, bee's wax, salt, and the like. Communal reservoirs of these materials have been used in the past with the same problems.

As a consequence of this high potential for contamination, the multiple dipping of body parts into a common reservoir, by different consecutive users, has already been outlawed in many countries. This is especially true where the paraffin applique is employed for hair removal applications. However, anywhere a heated wax pot is being employed cosmetically with customers, there is currently an ongoing and intense industry discussion relating to the possible hygiene concerns with current paraffin wax application methods.

Further, from a marketing standpoint with patrons of establishments providing waxing treatments, the mere thought of someone else's feet or hands or body parts having been dipped into the same wax reservoir as the next client, can be disgusting. The thought of another person's hair, skin, germs, or even DNA floating in the reservoir of warm wax is more than enough to discourage many patrons from undergoing the procedure.

As a consequence, the beauty industry has either had to discontinue a very profitable procedure, or, provide individualized wax reservoirs which are then discarded. These individual treatments and subsequent disposal of the wax reservoir contents, severely increases the cost of the procedure and is not very ecological in practice.

As such, there is an unmet need for a method and apparatus for providing individual portions of warmed paraffin or material with similar characteristics, for cosmetic and medical treatments. Such a method and device should provide the hygiene and convenience which will encourage more clients to willingly indulge in much desired paraffin treatments. Such a method should provide for quick, easy, and most importantly, hygienic, wax solutions and similar materials which may be applied to the skin of clients. Such a method and device should also allow for widespread standardized use so that clients become familiar with it and feel safe, and, establishments may offer standardized services and order standardized supplies to provide them.

SUMMARY OF THE INVENTION

The device and method herein disclosed and described achieves the above-mentioned goals and objects, through the provision of individualized paraffin wax portions, or other materials used to temporarily coat the body for masks and facials. The material provided herein is provided in self-heating containers which are adapted in a dimension to accommodate the body part being treated. It should be noted, that the use of the term paraffin and wax herein, is not intended to limit the method and device to this type of wax, but is employed for descriptive purposes. While paraffin wax is currently the industry standard for use in dipping reservoirs for patrons desiring waxing treatments, it is envisioned that those skilled in the art, especially upon reading this application which addresses hygiene and standardization and self-heating, will no doubt discern other materials which may be employed to temporarily coat the skin of users in a similar fashion with similar results. Such similar skin and body enhancement materials used for coatings on the skin include mud, oil, bee's wax, salt, and other materials which hold heat well and impart a cosmetic quality to the skin. Any and all such materials which might be employed in place of paraffin wax as stated herein, are anticipated within the scope of this application.

In a first preferred embodiment of the device and method herein, the paraffin wax or other material for skin coating is provided in containers. The individual containers are adapted in shape and dimension to accommodate and surround individual body parts of the user being treated. For instance, in the treatment of the hands, the container housing the wax used for the coating has the shape of a mitt or glove which will contain a supply of wax and surround the hand of the user when inserted. In the case of the feet, the container housing the wax is shaped like a booty or slipper and once warmed will easily slip over the user's foot and provide a wax coating and concurrently a barrier preventing the wax from spreading. The containers thus will mount over and on the body part being treated and maintain their position on the body part due to the shape and size of the containers used.

In preferred modes of the method and apparatus disclosed, means for heating the container-housed paraffin wax is through the employment of an exothermic liner or pouch which is adapted to surround and warm the body-part-shaped pouch surrounding the wax reservoir. Throughout the lining of the surrounding exothermic pouch, there is positioned an exothermic membrane, which once activated, will evenly heat the wax contents placed inside the pouch to a preset temperature. The exothermic reaction is activated either by pulling a tag or applying pressure to a designated point which mixes the contents to initiate a reaction or other means to initiate such a reaction that would occur to those skilled in the art.

The wax contents for each such body-part-shaped pouch are provided within the internal cavity of the wax container which is engaged within the disposable exothermic heating pouch by placing the wax within a plastic or other bag adapted to handle the heat. The wax container will be filled to a specific level preferably with scented paraffin wax.

In an especially preferred mode of the device and method, both the exothermic heater pouch and the wax container pouch are concealed within an individual box like structure. Each box will contain one completely sealed exothermic heater pouch and will provide protection to the heater pouch from being accidentally activated during transport or otherwise. When the lid of the box is opened to provide access to the exothermic heater pouch for activation, a flap is also unfolded. The flap is engaged with a neck of the heater pouch such that opening the box flap positions the discharge end of the neck facing vertically to thereby form an exhaust or chimney where steam, preferably with a pleasant fragrance, will exhaust once the exothermic pouch is activated.

Abutted against both sides of the heater pouch are the envelopes, made of a heat resistant plastic, holding the wax. For the hand application a heat resistant plastic glove in the shape of a hand or mitt is employed. This hand shaped plastic glove is pre filled with paraffin wax containing ingredients nourishing to the skin. One pre filled glove is folded and then inserted into each of the spaces formed adjacent to both the top and bottom of the exothermic pouch. The same procedure applies to the foot application except in this case a pre filled plastic booty in the shape of a foot is used.

In use, either a chemical bead is broken inside the exothermic pouch to start the reaction or a tab located at the top of the neck or chimney is pulled. However, other well known conventional means of initiating such a reaction may be utilized. Once the exothermic pouch is activated, it in turn heats the gloves/booties or facial wax which has been placed in the spaces adjacent to the exothermic pouch.

The wax in the body part shaped containers is heated to the correct temperature which as noted is currently substantially 53 degrees Celsius. Once so heated, the patrons hands or feet are inserted into the body part shaped container for the application process. After approximately twenty minutes the cotton mitts or booties or other body shaped container is removed. It is then returned back to the box where the expired exothermic pouch lies, the box is closed and the whole box is discarded. The facial application proceeds essentially in the same manner, however since it is not heated in pairs, the exothermic pouch is adjoined to it using one envelope space in a covering for the pouch.

The device and method may also be provided without the box by simply providing the pre-filled packages adapted in shape to the appropriate body part, along with an exothermic pouch adapted to position the body shaped packages holding the wax, next to the exothermic pouch. While not providing the protection of the box, nor the direction of the exhausting steam or fumes on opening, this mode of the invention still provides individualized wax in containers adapted to allow a surrounding of the body part such as the hand or foot by warm wax.

In use in all modes, the disposable exothermic pouch containing the wax housed in adjacent located body-part-dimensioned container, may be upstanding or horizontally positioned. It is then activated and within minutes the wax inside the pre filled plastic insert is melted to approximately 53 degrees Celsius. There may be an indicator on the pre filled insert, preferably visually displaying a color change when the desired temperature of the heated wax is achieved. Inks for indicia may be employed that change with temperature to achieve this indicator.

Once the desired temperature is achieved, the pre filled wax containing insert is removed from the exothermic pouch. Thereafter, the hands or feet or other body part being treated may be safely placed inside the shaped insert. Once so inserted, the paraffin wax is then gently massaged and dispersed around the hands or feet and then a seal is locked high above and around the wrist or ankle. While still inside the pre filled and heated wax-filled insert, the hands or feet are then placed inside the towelling or similar mitt or booty to help maintain the temperature of the wax for the time duration.

Thereafter, the towelling and plastic type mitt or booty is removed and the wax is then gently peeled off the hands/feet. The external towelling providing the mitt or booty may be laundered and reused, however the used disposable exothermic pouch provided to heat the wax, along with the individual wax container is disposed.

In this fashion, each individual treatment may be correctly and quickly heated and employed. More importantly, the client is assured of a sterile environment and sterile application of the wax material which is both healthful and reassuring to thereby encourage use.

In another mode of the device, self heating facial wraps will be presented in the shape of a mask with perforated holes, pre filled with paraffin. Once heated, using the adjacent-located disposable exothermic pouch, the facial wrap may be removed and engaged upon the face over a soft fabric protective mask which is first placed on the face. Optionally, the soft protective layer may be laminated or attached to one side surface of the pre filled facial wrap.

With the facial wrap warmed by the exothermic reaction, it is then placed upon the user's face. Once so placed, a pressing on the wrap releases the paraffin through the perforated holes allowing it to communicate into the protective fabric. The result is a warm luxurious feeling to the face of the user along with the aforementioned benefits of the wax treatment.

In another mode of the device and method, the wrap engaged to the body after exothermic heating in a pouch, can be provided by continuous sections of a pre filled elongated wax container which may be cut to length and employed to wrap and treat other body parts where desired. In this mode, the elongated container would be measured to wrap around an arm, leg, or other body position. A section would be cut and then warmed exothermically in a pouch. The section would then be engaged to the body of the user and the wax excreted into the protective layer through holes in the wax container.

In all modes of the method and apparatus herein, the user or client is provided with the assurance that his or her wax treatment is individualized and has no risk whatsoever of contamination of the wax by a prior user. This will not only meet most health standards in most venues for salons, it will maintain the health of the clients receiving the treatment even in venues where health standards are lax.

With respect to the above description, it is to be understood that the invention is not limited in its application to the details of construction and to the arrangement of the components in this specification or illustrated in the drawings. The device and method herein described for individualized paraffin treatments, are capable of using other materials than paraffin with the same properties, and other embodiments and of being practiced and carried out in various ways which will be obvious to those skilled in the art upon reading this disclosure. Also, it is to be understood that the phraseology and terminology employed herein are for the purpose of description and should not be regarded as limiting.

As such, those skilled in the art will appreciate that the conception upon which this disclosure is based may readily be utilized as a basis for the designing of other structures, methods and systems for carrying out the several purposes of the present disclosed individualized wax treatments using exothermically heated body dimensioned wax containers. It is important, therefore, that the claims and disclosure herein be regarded as including such equivalent construction and methodology insofar as they do not depart from the spirit of the present invention.

It is an object of this invention to provide an individualized wax treatment for users which is clean and eliminates potential contamination from multiple users.

It is an additional object of this invention to provide such a wax treatment apparatus and process which employs wax containers that are heated exothermically and which are dimensioned to conform to the shape of the body of the user where they are to be used.

These together with other objects and advantages which become subsequently apparent reside in the details of the construction and operation as heretofore described with reference being had to the accompanying drawings forming a part thereof, wherein like numerals refer to like parts throughout.

BRIEF DESCRIPTION OF DRAWING FIGURES

DETAILED DESCRIPTION OF PREFERRED EMBODIMENTS

Figure 2:
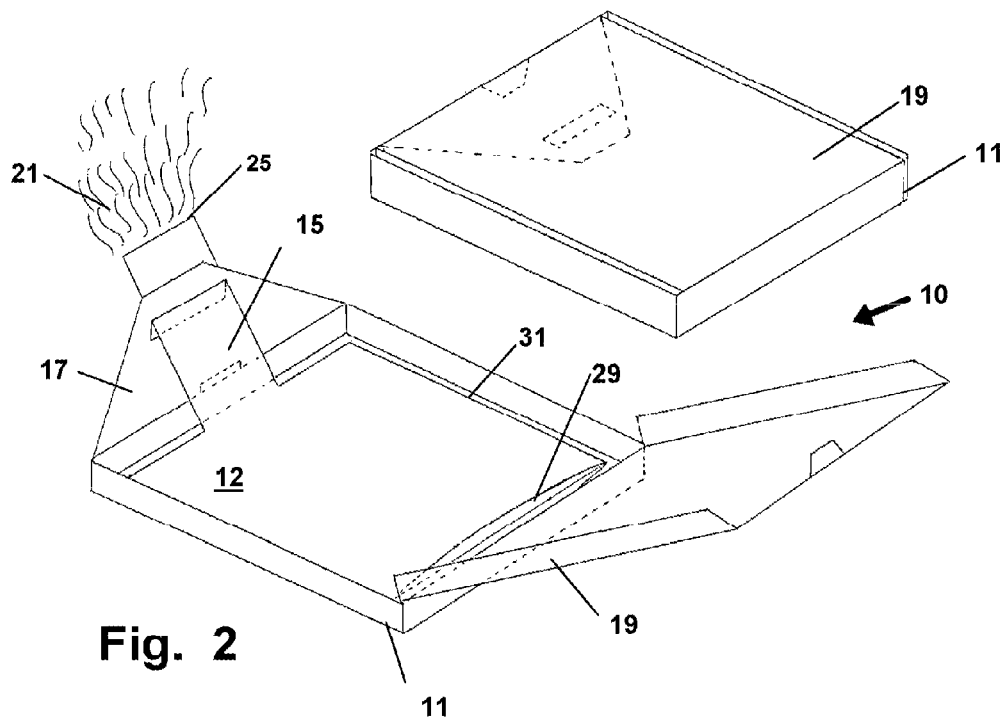
FIG. 2 shows the device as an exothermic pouch employed to heat a face mask dimensioned wax container having apertures to communicate heated wax to a protective layer.

Referring now to the drawings of FIGS. 1-6 showing the wax or other coating material treatment device 10 employed in the method herein, wherein similar parts are identified by like referenced numerals which may be found in one or more of the drawings.

Figure 1:
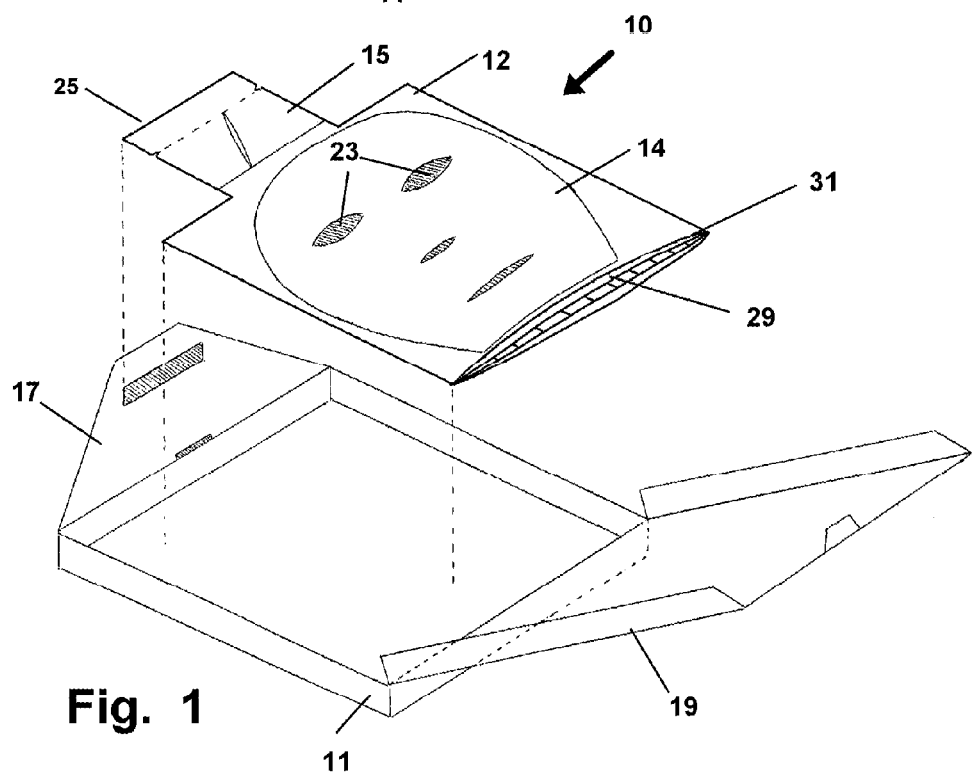
FIG. 1 shows the box employed in combination with a favored mode of the device and method herein and its engagement with the exothermic pouch to vent it during use.

In FIG. 1 there is depicted a box 11 adapted to engage a typical exothermic pouch 12 for heating individualized portions of paraffin held in a wax container 14 held in a cavity 29 which is preferably shaped in a dimension to accommodate the body part being treated such as a face, foot, or hand. A tail portion 15 of the pouch 12 is engaged with a flap 17 of the box 11 such that when the lid 19 is opened the flap 17 positions the tail portion 15 substantially upright to vent vapors 21 from an exhaust aperture 25 in the tail portion 15. Scents may be added to enhance the vapors 21. If employed without the box as in FIG. 5, the tail portion 15 would simply vent the vapors 21 while held elevated or lying down. However the box 11 is particular preferred to protect the pouch 12 during storage and makes it easier for the user to deploy.

Figure 5:
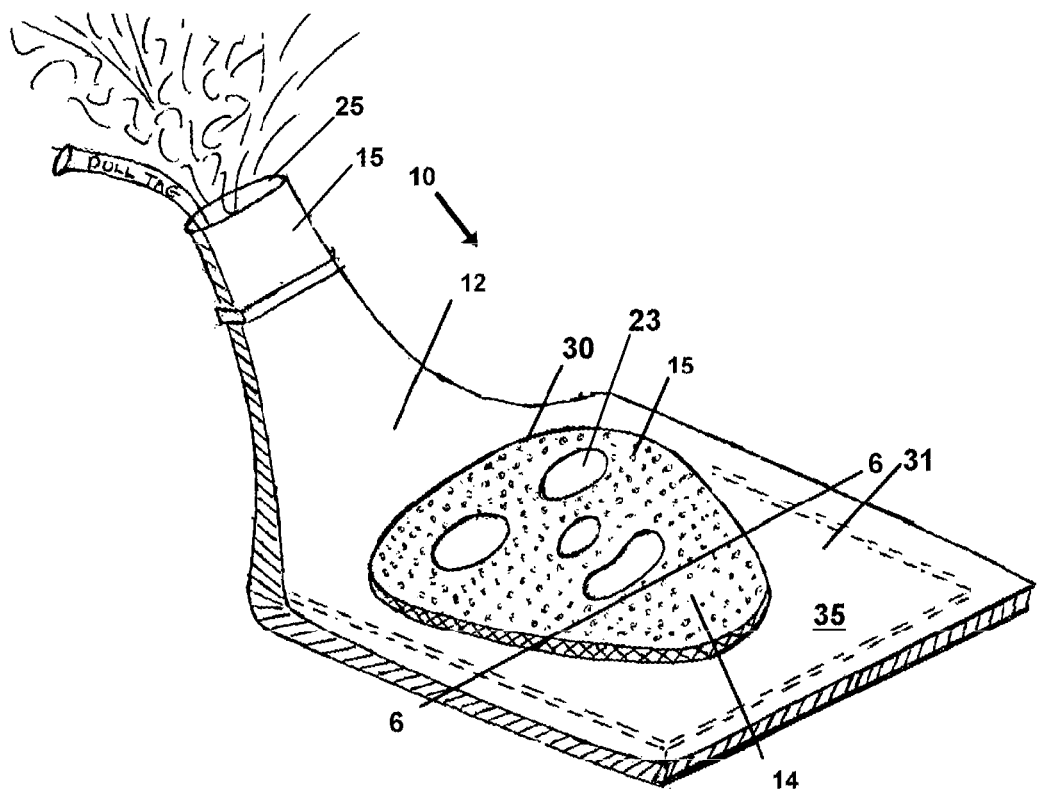
FIG. 5 shows the device as an exothermic pouch without the box, employed to heat a face mask dimensioned wax container having apertures to communicate heated wax to a protective layer.

The container 14 in the facial mode of the device 10 as in FIGS. 1 and 5, holds a planar facial mask that is made using a scrim 30 of latex or similar non toxic material. The scrim is pre soaked with paraffin and allowed to harden. Facial apertures 23 for the eye, nose and mouth holes have been cut through the scrim and wax prior to placement next to a pouch 12 for heating. Once the pre soaked paraffin mask has melted, it is placed upon the patron's face over a protective cotton gauze or pad of similar material also in the shape of a mask which has already been placed onto the face of the patron. By gently pressing downward, the melted paraffin is released from the latex or similar scrim and through the protective gauze onto the patron's face. The paraffin hardens in the shape of the patron's face and is removed after approximately twenty minutes leaving a beautiful look and soft feeling to the skin. The facial mask once formed on the scrim and with apertures 23 cut, is positioned either in a cavity 29 adjacent to the pouch 12, or upon the sidewall of a exothermic pouch 12 where it can be activated in a conventional fashion to warm the wax in the wax container 14.

Figure 3:
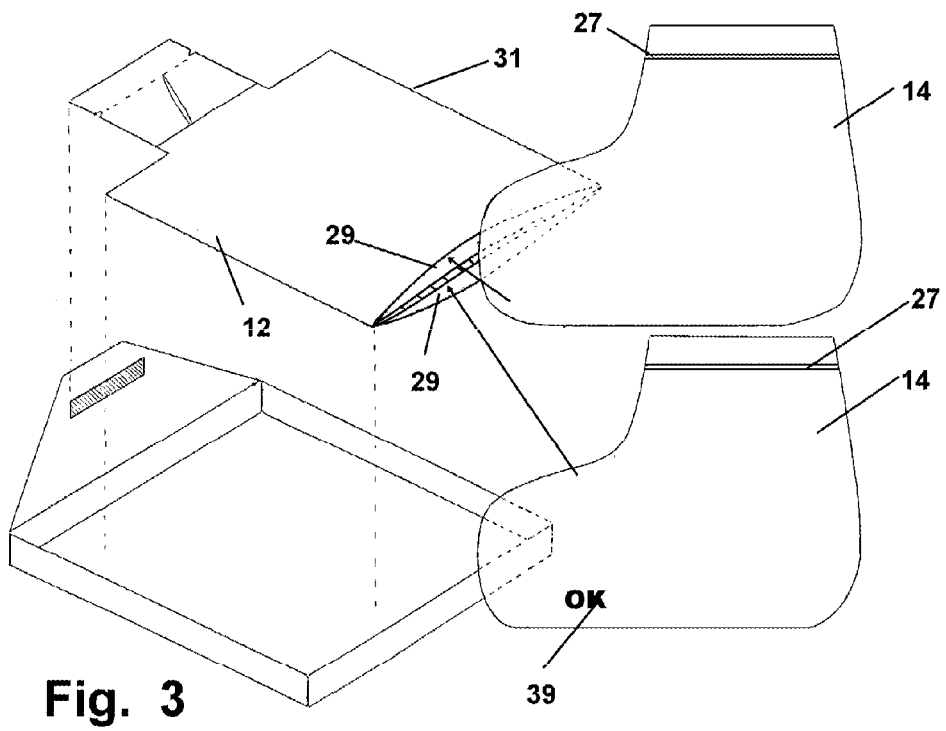
FIG. 3 depicts a wax container dimensioned for foot engagement being in the shape of a foot.
Figure 4:
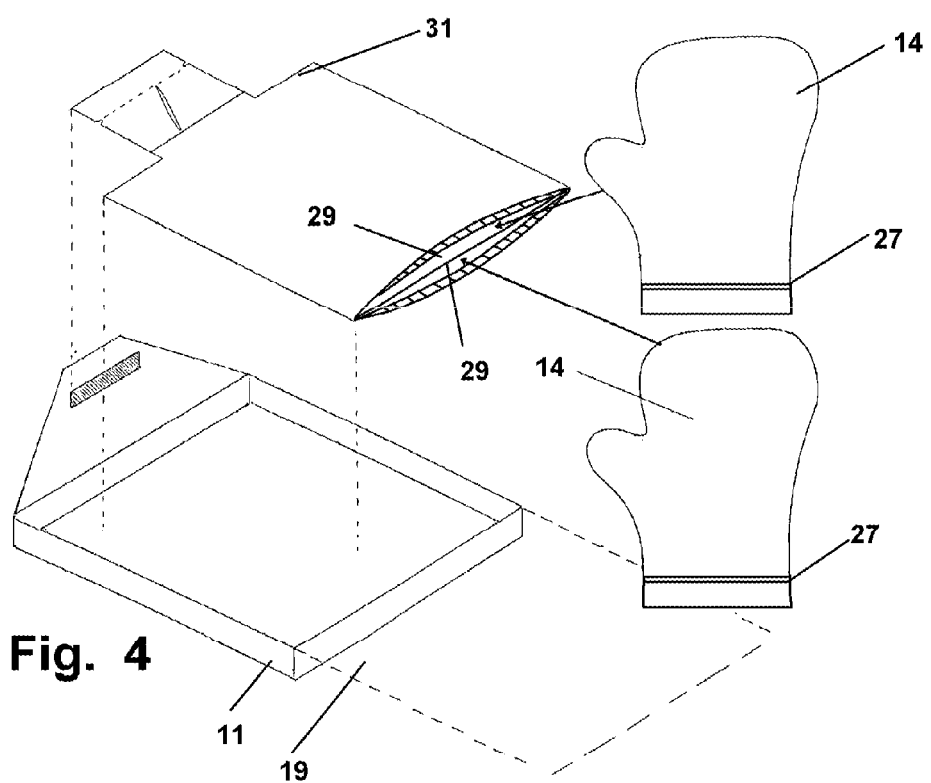
FIG. 4 depicts a wax container dimensioned for hand engagement in the shape of a mitt.

In FIG. 3 there is shown a wax container 14 adapted to engage over a foot, by shaping the container 14 in the shape of a booty or slipper. In FIG. 4 the wax container 14 is shown adapted to engage over a hand by making the container 14 in which the paraffin is held prior to heating by an exothermic pouch 12, in the shape of a mitt. The containers have a seal 27 formed on one end to maintain the wax therein which is opened to insert the body part.

In FIGS. 1-4 there is shown a manner in which the device 10 situates the paraffin container 14, adapted to engage over a body part, by adapting the container to hold wax in the shape of a face mask, foot, hand, or other body part. As shown, in FIGS. 1-3, the exothermic pouch 12 is positioned in a center position and means to hold the paraffin container 14 adjacent to the side of the exothermic pouch is provided by cavities 29 formed adjacent to the pouch 12 using a plastic or fabric surrounding structure 31 to the centrally located exothermic layer 18 of the exothermic pouch 12. Of course other means to maintain the paraffin container 14 shaped like a body part, adjacent to the exothermic layer 18 and pouch 12 may be used and are anticipated. Currently the provision of cavities 29 using a surrounding structure 31 formed as part of the exothermic pouch 12 works well to communicate heat from both sides of the exothermic layer 18 concurrently to the wax in abutted containers 14. The cavity 29 may be on one side of the exothermic pouch as in FIG. 5 where an attached flap 35 provides the means to abut the container 14 to the exothermic layer 18 of the pouch 12. Or as shown in FIG. 4, two exothermic layers 18 might be provided on both sides of two cavities 29. The overriding factor being to provide a means to abut the container 14 with the wax, adjacent to the heat from the pouch 12 and exothermic layer 18.

Figure 6:
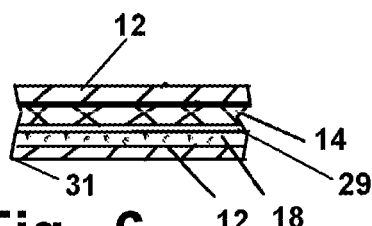
FIG. 6 shows a sliced view through a heating pouch for the wax containers showing the exothermic layer typical of all modes.

There is seen in FIG. 6, a slice through line 6-6 of FIG. 5, which shows one mode of a warming or exothermic pouch 12 showing the exothermic layer 18 lining a sidewall forming the pouch 12. As noted, the layer is activated in a conventional fashion to initiate heating of the housed wax container 14. Further, it is preferred, that means to visually alert the user to the correct temperature being achieved such as temperature sensitive inks for indicia should be employed that change with temperature to achieve this indicator 39.

Currently the use of an exothermic pouch 12 works especially well for the warming of the containers 14 with no other mechanical or electrical means for heating. However, it is anticipated that the exothermic layer 18 might be substituted for a gel or chemical layer adapted to heating by microwave or other means and that a pouch of that fashion might also be used with slightly less utility but also without the need for the exothermic reaction. Other means to provide a heat source that may be abutted to containers 14 shaped to hold wax in the shape of body parts are thus anticipated within the scope of this invention.

While all of the fundamental characteristics and features of the individualized wax treatment device and method herein have been shown and described, with reference to particular embodiments thereof, a latitude of modification and various changes and substitutions are intended in the foregoing disclosure and it will be apparent that in some instances, some features of the invention may be employed without a corresponding use of other features without departing from the scope of the invention as set forth. It should also be understood that various substitutions, modifications, and variations may be made by those skilled in the art without departing from the spirit or scope of the invention. Consequently, all such modifications and variations and substitutions are included within the scope of the invention as defined by the following claims.

What is claimed is:

1. An apparatus for provision of individualized portions of skin coating material for skin masks or facials, comprising:
   a flexible container having an internal cavity and external surface;
   said container having an access aperture and having releasable seal for said aperture;
   a portion of skin coating material stored within said internal cavity;
   means to heat said material in said internal cavity of said container to a predetermined temperature; wherein said means to heat said material is a pouch; wherein said pouch comprises: a tail portion, and an exothermic material, said tail portion having a vent at a distal end for venting fumes produced by said exothermic material when activated by a user;
   means to abut a portion of said external surface of said container, against said means to heat said material;
   said internal cavity dimensioned larger than, and shaped similar to, an exterior shape of a foot or hand; and
   a box, said box having an internal cavity sized to hold said apparatus, said cavity accessible by opening a lid;
   said box having a flap portion deployable from said internal cavity of said box to an upright position; and
   said tail portion of said pouch engaged to said flap wherein said vent is elevated above said pouch when said flap is in said upright position;
   whereby said foot or hand is inserted into said internal cavity through said access aperture and therein is surrounded by a sanitary portion of said coating material heated to said temperature in an individual portion thereof.

2. The apparatus for provision of individualized portions of skin coating material of claim 1 wherein said means to heat said material in said internal cavity is a layer of exothermic material contained in a pouch which may be user-activated to produce heat.

3. The apparatus for provision of individualized portions of skin coating material of claim 2 wherein said means to abut a portion of said external surface of said container against said means to heat said material comprises:
   a cavity formed by a wall extending from two points on said pouch, said cavity sized to position said portion of said external surface against said pouch, whereby heat from said exothermic material communicates from said pouch and provides a warming of said coating material to said predetermined temperature.

4. The apparatus for provision of individualized portions of skin coating material of claim 3 wherein said coating material is paraffin wax.

5. The apparatus for provision of individualized portions of skin coating material of claim 3 additionally comprising:
   visual means to signal said predetermined temperature located on one of said external surface of said container or said wall extending from said pouch.

6. The apparatus for provision of individualized portions of skin coating material of claim 4 additionally comprising:
   visual means to signal said predetermined temperature located on one of said external surface of said container or said wall extending from said pouch.

* * * * *